(12) United States Patent
Christiansen et al.

(10) Patent No.: US 11,529,046 B2
(45) Date of Patent: Dec. 20, 2022

(54) TONGUE MANEUVERING APPARATUS AND METHOD OF USE

(71) Applicant: Black Diamond Creations, LLC, St. George, UT (US)

(72) Inventors: Brett D. Christiansen, St. George, UT (US); Christopher B. Christiansen, St. George, UT (US); James B. Christiansen, St. George, UT (US); Clancy B. Christiansen, St. George, UT (US); Candice S. Christiansen, St. George, UT (US); Bryce B. Christiansen, St. George, UT (US); Susan G. Christiansen, St. George, UT (US); Phillip Dietz, St. George, UT (US); Cathy Christiansen, St. George, UT (US); Kami Christiansen, St. George, UT (US)

(73) Assignee: Black Diamond Creations, LLC, St. George, UT (US)

( * ) Notice: Subject to any disclaimer, the term of this patent is extended or adjusted under 35 U.S.C. 154(b) by 92 days.

(21) Appl. No.: 17/091,726

(22) Filed: Nov. 6, 2020

(65) Prior Publication Data

US 2021/0127966 A1 May 6, 2021

Related U.S. Application Data

(60) Provisional application No. 62/931,605, filed on Nov. 6, 2019.

(51) Int. Cl.
| | | |
|---|---|---|
| A61B 1/32 | (2006.01) |
| A61B 1/24 | (2006.01) |
| A61B 17/02 | (2006.01) |
| A61B 13/00 | (2006.01) |
| A61B 17/00 | (2006.01) |

(52) U.S. Cl.
CPC ............... *A61B 1/24* (2013.01); *A61B 13/00* (2013.01); *A61B 17/0218* (2013.01); *A61B 2017/00477* (2013.01); *A61B 2017/00561* (2013.01); *A61B 2017/0225* (2013.01)

(58) Field of Classification Search
CPC combination set(s) only.
See application file for complete search history.

*Primary Examiner* — Sameh R Boles
(74) *Attorney, Agent, or Firm* — Gurr Brande & Spendlove, PLLC; Robert A. Gurr (57) ABSTRACT

A tongue maneuvering apparatus has a body, a first attachment site, and a second attachment site. The body includes a bulb, a tongue receiving portion, a tongue aperture, and a slot. The body may be a thin, pliable plastic, such as silicone, so as to create proper suction with the tongue when inserted into the tongue receiving portion. A healthcare provider is able to extend and manipulate a patient's tongue so as to clearly view the mouth and throat without activating the gag reflex and maintaining control of the tongue by the provider.

19 Claims, 15 Drawing Sheets

TONGUE MANEUVERING APPARATUS AND METHOD OF USE

CROSS-REFERENCE TO RELATED APPLICATIONS

This application claims the benefit of U.S. Provisional Application Ser. No. 62/931,605, filed on Nov. 6, 2019, which is incorporated herein by reference.

TECHNICAL FIELD

The present disclosure relates to a tongue control device. More particularly, the present disclosure relates to a tongue maneuvering apparatus that suctions to a tongue for controlling the movement of the tongue during a medical or dental procedure/examination.

BACKGROUND

Tongue depressors have been used for several centuries to evaluate the mouth and throat during medical and dental examinations. Early tongue depressors were made of metal, but due to the time to make the device, the cost, and sterility issues, they were replaced by simple disposable wooden depressors. Today, these disposable wooden depressors can be found in the hands of healthcare providers in every corner of the globe. The wooden tongue depressor is cost-effective and simple to use, which is why it has been used for so many years.

There have been many technological breakthroughs in medicine since the inception of the tongue depressor, and many medical devices have been improved. However, there have not been improvements to the wooden tongue depressor. In fact, the same tongue depressor that was used a hundred years ago is still used today. The wooden tongue depressor has not benefitted from the advances in technology like many other medical devices. While the wooden tongue depressor has many good attributes, there are many significant shortcomings.

When a healthcare provider introduces a tongue depressor into the mouth of a patient, the act of depressing the tongue can cause an uncomfortable and undesirable gag reflex, which is present in nearly all humans and may induce vomiting. In addition, many people induce a gag reflex with just the thought of a tongue depressor touching the back of their tongue. This often prevents a healthcare provider from ever using a tongue depressor on this group of people.

Further, the current tongue depressor does not allow a healthcare provider the control needed for many examinations and procedures. While the tongue can be flattened somewhat with the tongue depressor, the patient still has the ability, and often does, protectively and subconsciously, move the tongue up and back. This can completely block the healthcare provider from viewing the throat, tonsils, and back of the tongue.

Using the current tongue depressor requires the use of one hand at all times by the provider to hold the depressor in place, while the other hand is occupied with a light or a swab during a procedure or test. This limits the efficacy of such procedures and tests, potentially causing increased procedure time, contamination of testing specimens, and procedure complications. When a healthcare provider has both hands occupied, one hand on the depressor and the other hand holding, for example, a swab, it is difficult to visualize structures in the back of a non-illuminated throat. In order to visualize the structures of the throat, a separate light, often an otoscope, must be utilized to view the structures of the back of the throat when one of the healthcare provider's hands is not occupied with a tongue depressor or swab. Alternatively, the healthcare provider would always need an assistant to hold a light while performing a procedure.

Accordingly, there is a need for a tongue depressor that prevents a patient from experiencing a gag reflex, gives more control to the healthcare provider, frees the hands of the healthcare provider, and illuminates the back of a patient's throat. The present disclosure seeks to solve these and other problems.

SUMMARY OF EXAMPLE EMBODIMENTS

In one embodiment, a tongue maneuvering apparatus comprises a body, a first attachment site, and a second attachment site. The body comprises a bulb, a tongue receiving portion, a tongue aperture, and a slot. The body may be a thin, pliable plastic, such as silicone, so as to create proper suction with the tongue.

In one embodiment, a tongue maneuvering apparatus comprises a tongue depressor that is coupleable to the first attachment site.

In one embodiment, a tongue maneuvering apparatus comprises an anchor device and an illumination device. The illumination device comprises a first coupler for attaching to a first attachment site. The anchor device comprises a second coupler and a ring. The second coupler may attach to the second attachment site.

In one embodiment, a method of using the tongue maneuvering apparatus comprises placing a patient's tongue into a tongue aperture, displacing the air in the tongue maneuvering apparatus. Once the tongue is inserted, the tongue maneuvering apparatus is slid toward the back of the throat, on the tongue, until the frenulum is positioned in slot, thereby allowing proper suction of the tongue. After the tongue maneuvering apparatus is secured, via suction, a healthcare provider may move the tongue to a desired position to view the throat of the patient.

DETAILED DESCRIPTION OF EXAMPLE EMBODIMENTS

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

Tongue depressors have been used for centuries with little-to-no change. These tongue depressors often induce a gag reflex when used on patients. Other problems are also readily evident when using the tongue depressors found in the art, such as a lack of control. Often, the patient may move their tongue while a procedure is being performed, which makes a procedure difficult or impossible. In contrast, the tongue maneuvering apparatus described herein generally comprises a body with a tongue receiving portion and a bulb. A healthcare provider may place a patient's tongue inside the tongue receiving portion, with the bulb creating suction. Once the tongue maneuvering apparatus is in position, the healthcare provider has more control over the tongue, thereby decreasing the time of the procedure and reducing gag reflexes of the patient.

Figure 15:
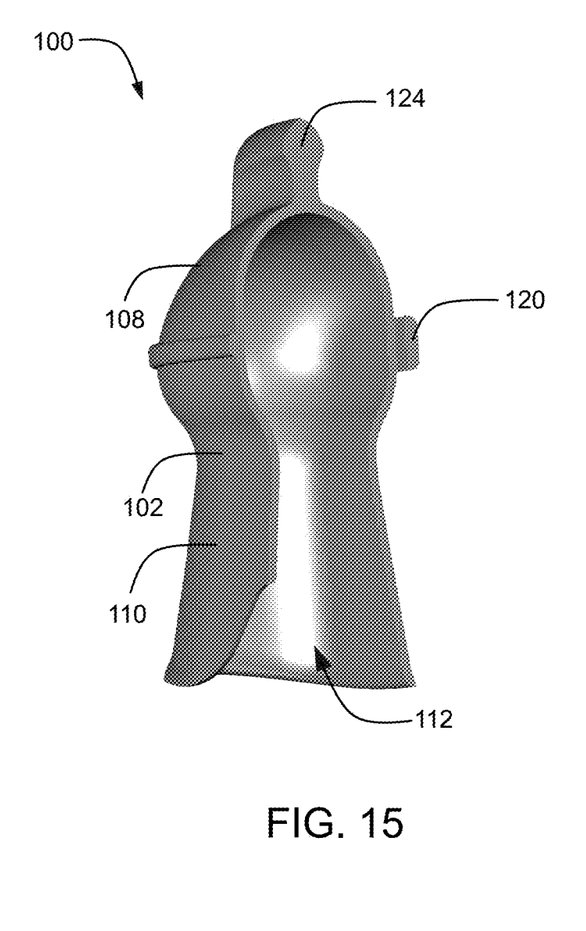
FIG. 15 illustrates a cross sectional view of a tongue maneuvering apparatus.

As shown in FIGS. 1-6, in one embodiment, a tongue maneuvering apparatus 100 comprises a body 102, a first attachment site 104, and a second attachment site 106. The body 102 comprises a bulb 108, a tongue receiving portion 110, a tongue aperture 112, and a slot 114. The body 102 may be a thin, pliable plastic, rubber, silicone, or other material so as to create proper suction with the tongue. It will be appreciated that the body 102 does not have to be a thin, pliable material but may also be a thicker material that can still create a proper suction with the tongue. In some embodiments, the body 102 may couple to the first one-third of the tongue to ensure a proper grip on the tongue. Alternatively, the body 102 may couple to more or less than the first one-third of the tongue so long as proper suction is created. The bulb 108 may be sealed so that air does not escape after being depressed to create suction with the tongue. For example, a healthcare provider would hold the apparatus 100 and instruct a patient to insert their tongue through tongue aperture 112 and into tongue receiving portion 110 (shown in FIG. 15), displacing the air with their tongue, which creates a suction on the patient's tongue.

With suction applied, the healthcare provider may grip the second attachment site 106, allowing the healthcare provider to pull the patient's tongue outward, exposing the throat and mouth for inspection. However, the control is not limited to pulling the tongue out. For example, the healthcare provider may manipulate the tongue in any direction. Accordingly, the healthcare provider is able to easily control and position the tongue. In contrast, the wooden depressor found in the prior art does not allow full control of the tongue. Without full control of the tongue, the patient often moves their tongue, intentionally or subconsciously, blocking the view of the mouth and throat. Often, a patient moves their tongue due to a gag reflex that comes from pressing the wooden tongue depressor on the back of the tongue. The tongue maneuvering apparatus 100 is a significant improvement over the wooden tongue depressor. In particular, the tongue maneuvering apparatus 100 does not activate the gag reflex. As a result, the healthcare provider may more easily, comfortably, and efficiently inspect the mouth and throat of a patient.

In addition, the body of the tongue maneuvering apparatus 100 may be different sizes to fit varying tongue sizes. For example, there may be a smaller (e.g., in width and depth) tongue maneuvering apparatus 100 so as to fit properly on a child's tongue. There may also be a medium, large, or any other sized tongue maneuvering apparatus 100 to provide proper fit and suction on a patient's tongue. In some embodiments, the tongue maneuvering apparatus 100 may also be color coded, where a specific color is associated with a specific size (e.g., blue is a large). Further, the tongue receiving portion 110 starts wide at the tongue aperture 112 and narrows as it proceeds to the bulb 108. The tongue aperture 112 may vary in size so as to receive a variety of shapes and sizes of tongues.

Figure 1:
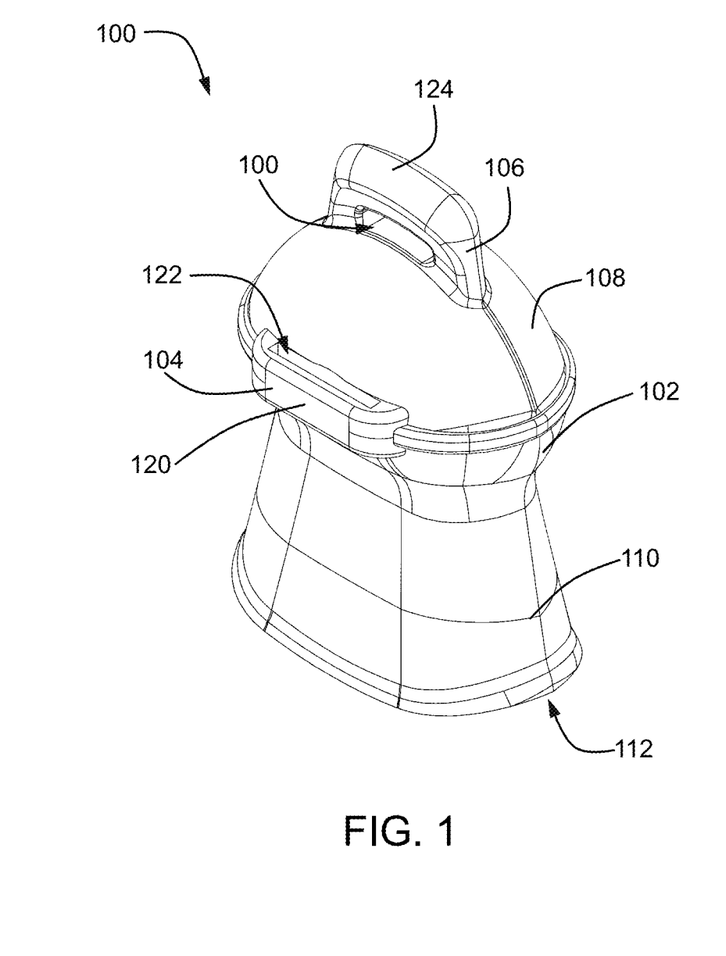
FIG. 1 illustrates a front, top perspective view of a tongue maneuvering apparatus.
Figure 2:
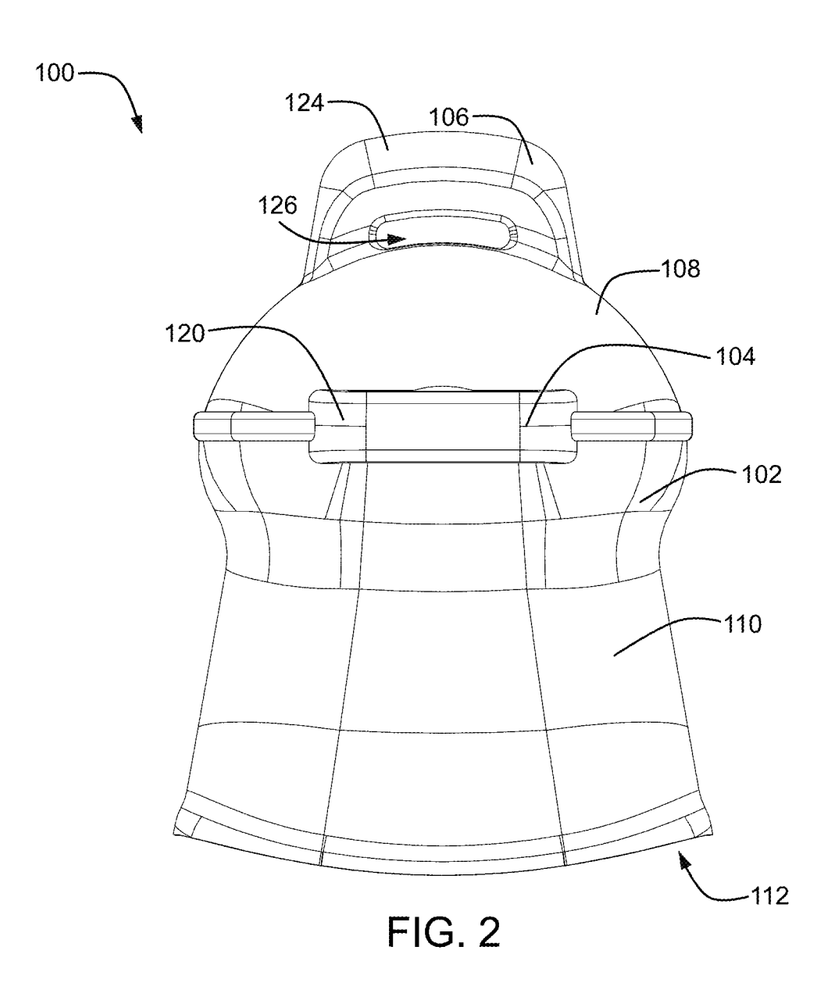
FIG. 2 illustrates a top plan view of a tongue maneuvering apparatus.
Figure 3:
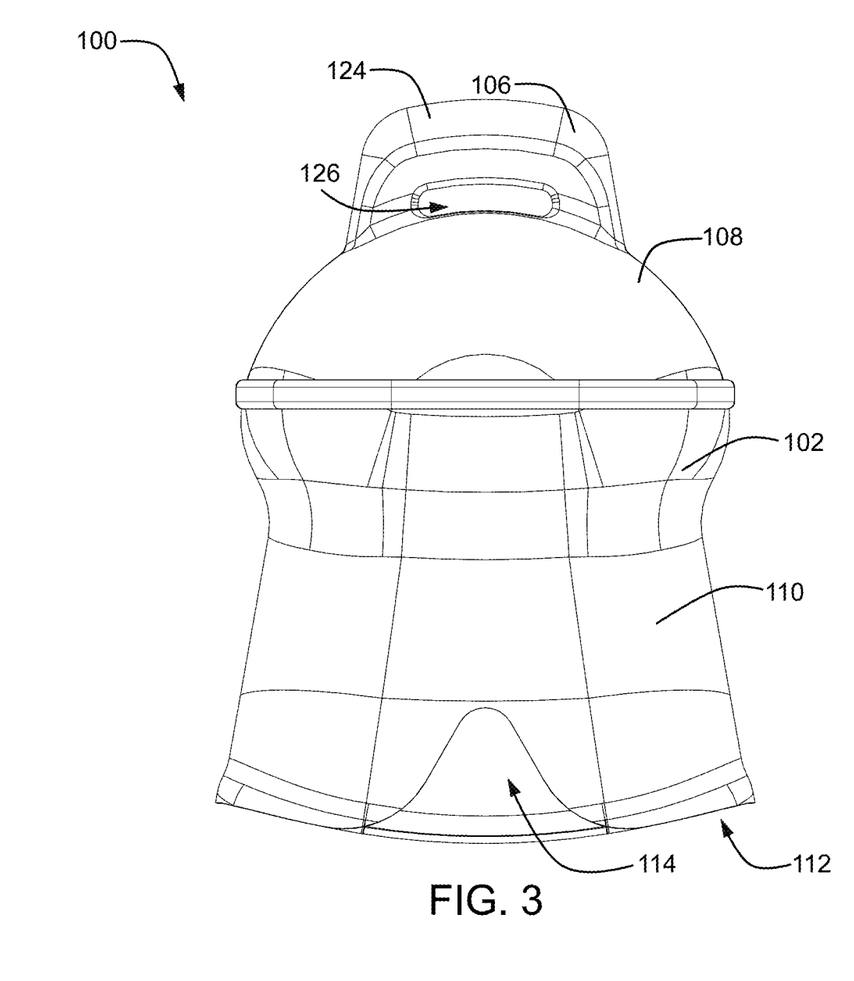
FIG. 3 illustrates a bottom plan view of a tongue maneuvering apparatus.
Figure 4:
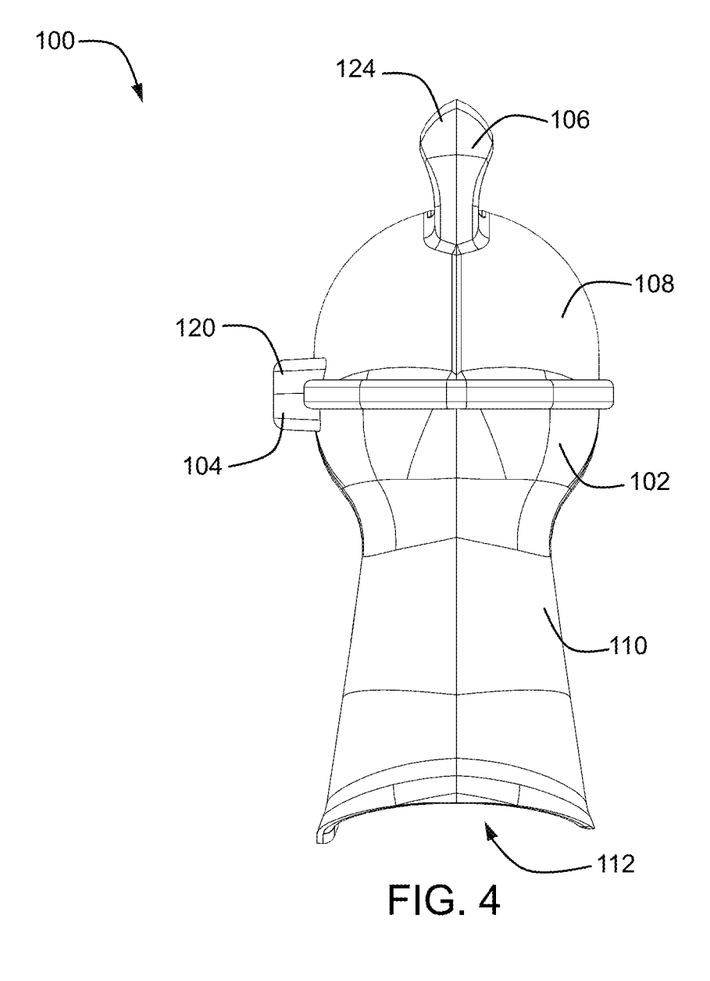
FIG. 4 illustrates a left side elevation view of a tongue maneuvering apparatus.
Figure 5:
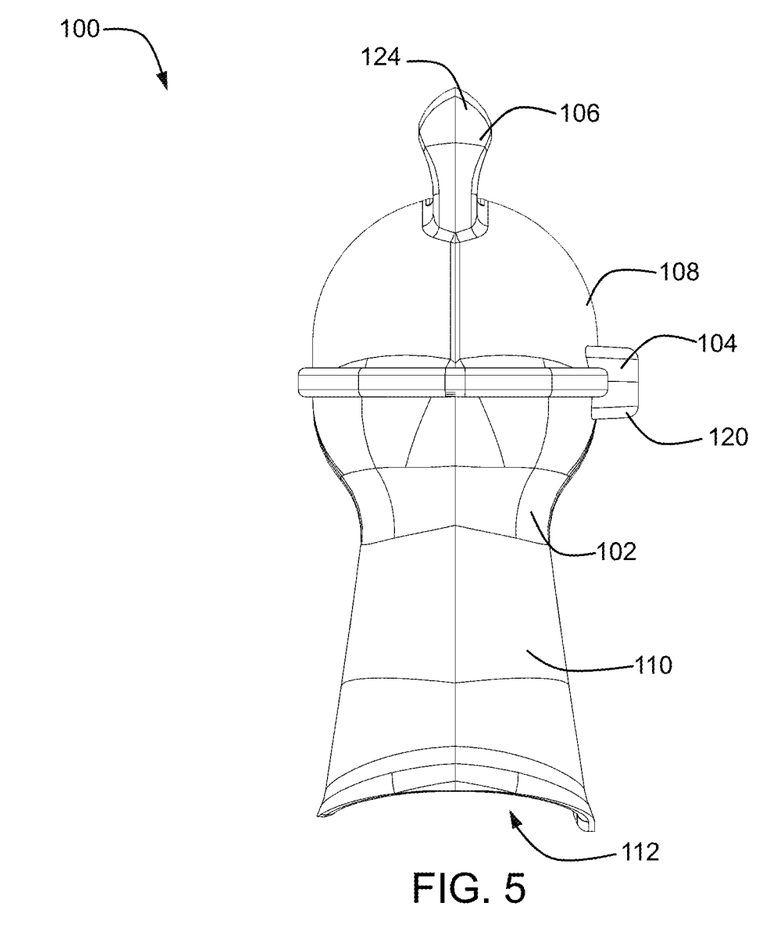
FIG. 5 illustrates a right side elevation view of a tongue maneuvering apparatus.
Figure 6:
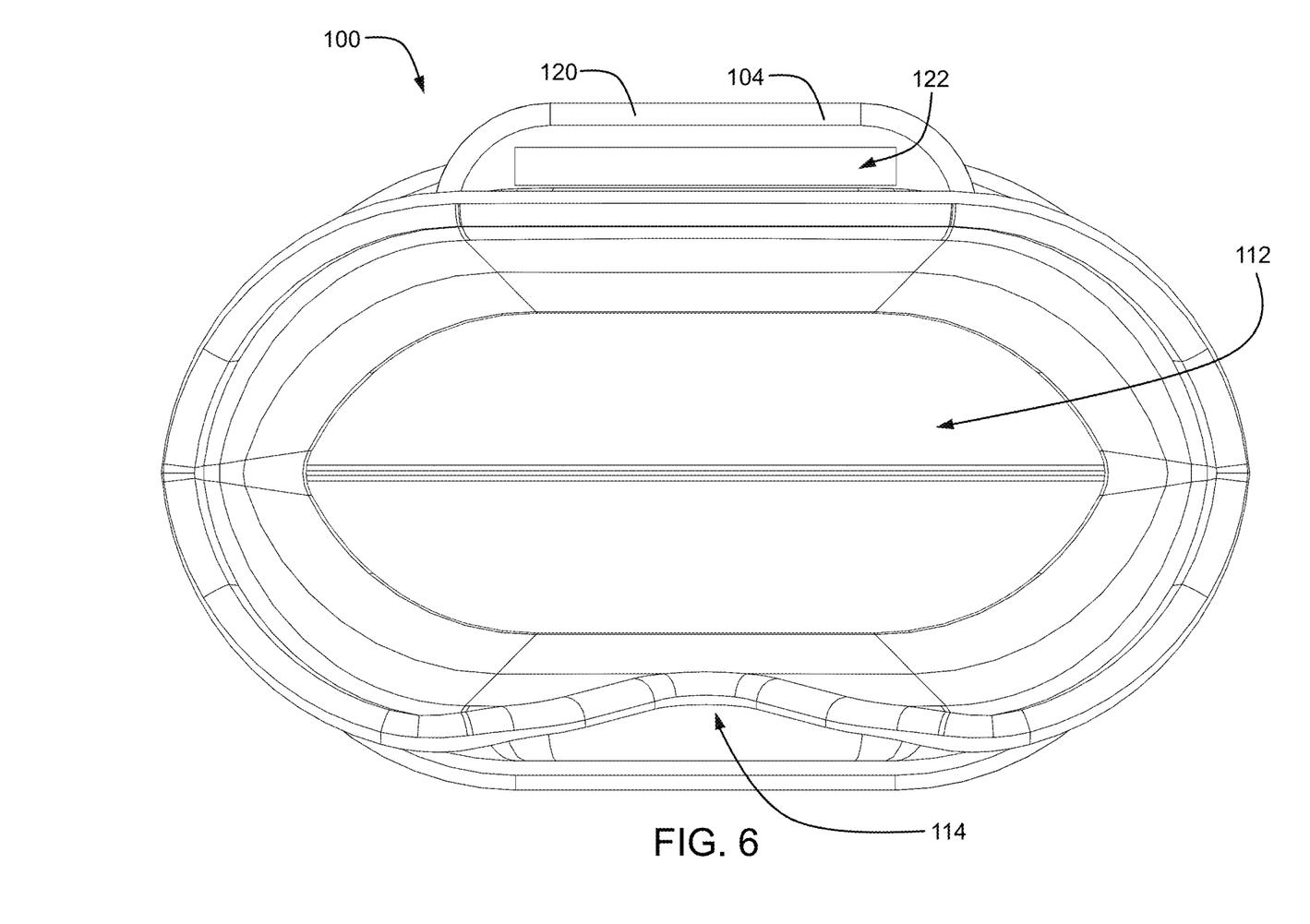
FIG. 6 illustrates a rear elevation view of a tongue maneuvering apparatus.

As illustrated in FIG. 3, the body 102 further comprises the slot or cutout 114. The slot 114 may be v-shaped. However, the slot 114 is not limited to a v-shape and may be u-shaped or any other shape to receive the bottom of the tongue, such as the frenulum of the tongue. It will be appreciated that the slot 114 allows the tongue maneuvering apparatus 100 to suction to a necessary portion of the tongue. If the slot 114 is not present, for some individuals, the tongue maneuvering apparatus 100 will not be able to receive a large enough portion of the tongue to create proper suction. However, while the slot 114 is shown, in some circumstances the slot 114 may not be necessary to create proper suction to the tongue. Therefore, in one embodiment, the slot 114 is not required.

Figure 14:
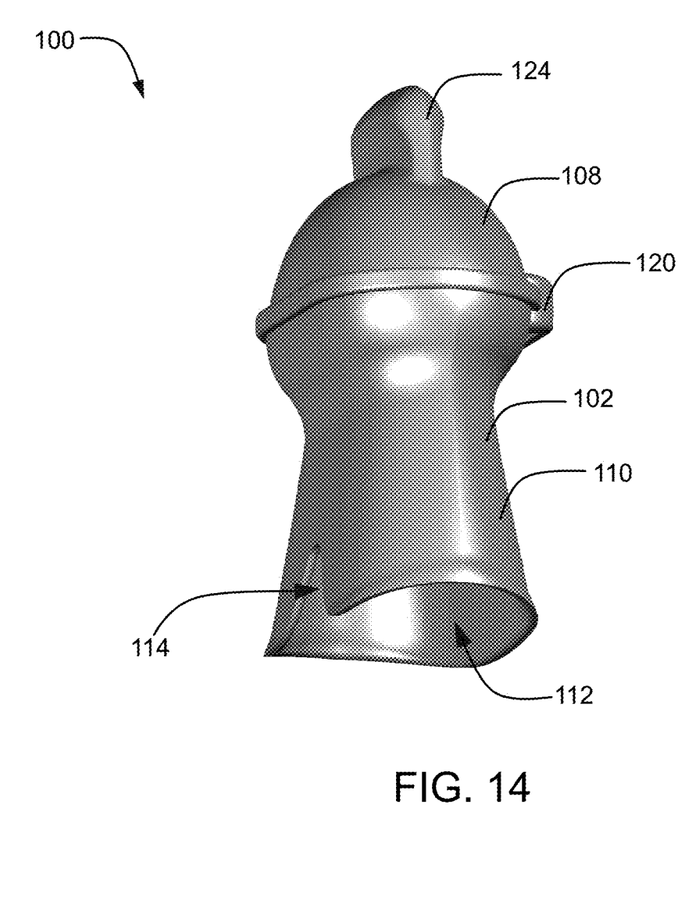
FIG. 14 illustrates a bottom, side perspective view of a tongue maneuvering apparatus.

The first attachment site 104 comprises a first protrusion 120 with a first aperture 122 positioned between the first protrusion 120 and the body 102. The second attachment site 106 comprises a second protrusion 124 with a second aperture 126 positioned between the second protrusion 124 and the body 102. The second protrusion 124 may assist a healthcare provider in manipulating and controlling a tongue. In other words, a healthcare provider may grasp the second protrusion 124, once the tongue is inserted into the tongue maneuvering apparatus 100, and move the tongue. While the second protrusion 124 is shown with the second aperture 126, it will be appreciated that, in some embodiments, the second protrusion 124 may not have an aperture (shown in FIG. 14).

Figure 7:
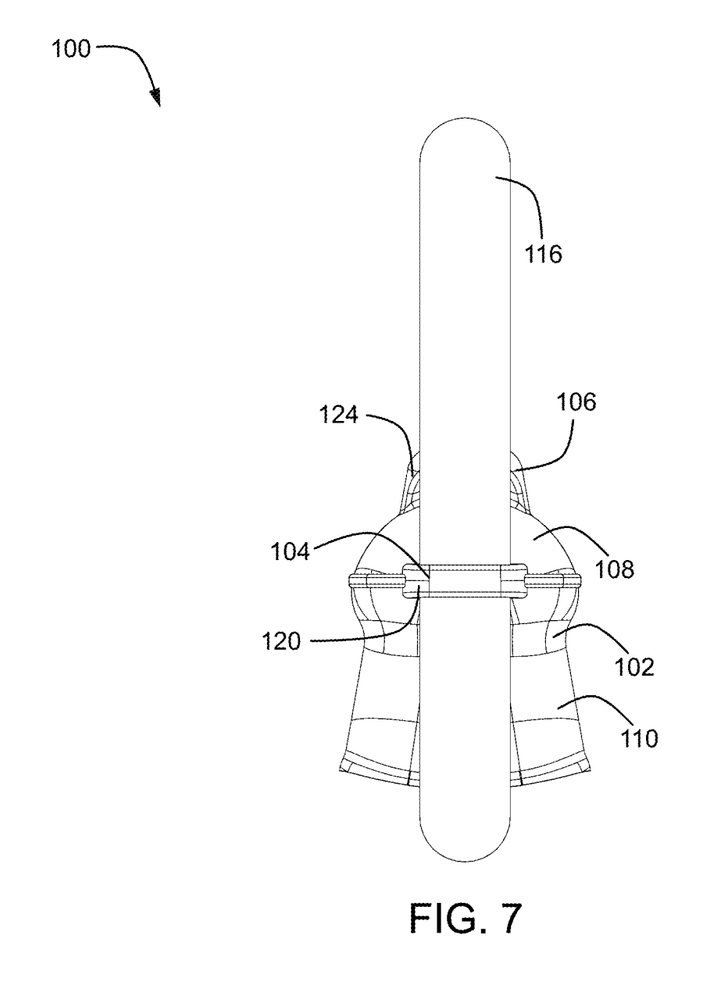
FIG. 7 illustrates a top plan view of a tongue maneuvering apparatus with a tongue depressor coupled to a first attachment site.
Figure 8:
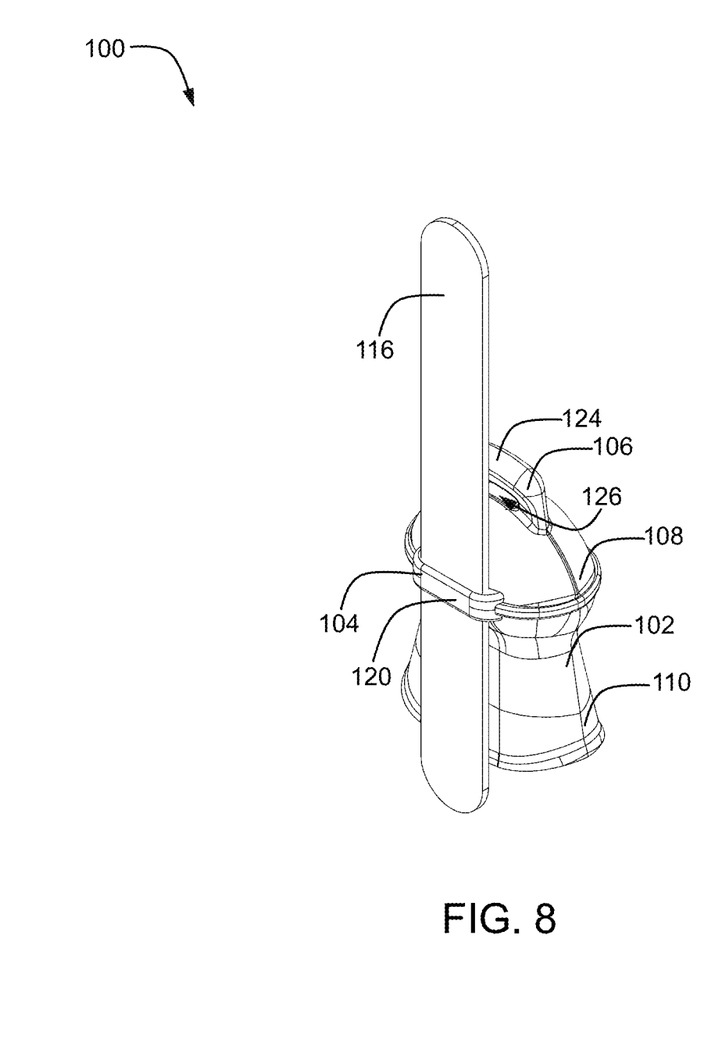
FIG. 8 illustrates a top, front perspective view of a tongue maneuvering apparatus with a tongue depressor coupled to a first attachment site.
Figure 9:
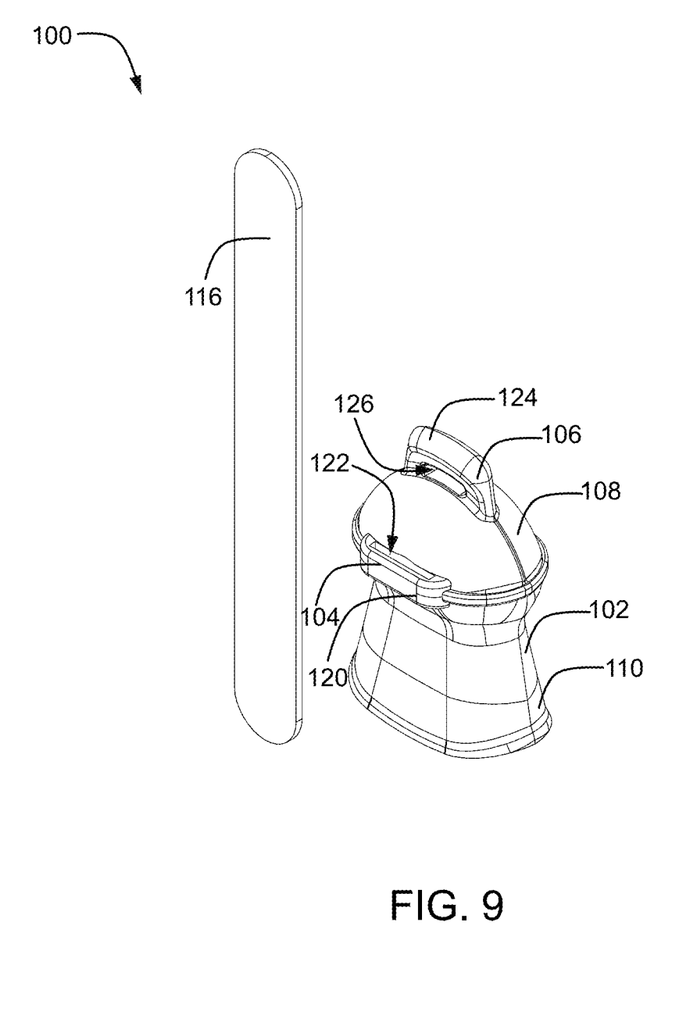
FIG. 9 illustrates a top, front perspective view of a tongue maneuvering apparatus with a tongue depressor decoupled from a first attachment site.

In one embodiment, as shown in FIGS. 7-9, the tongue maneuvering apparatus 100 may receive a tongue depressor 116 in the first attachment site 104. Specifically, the tongue depressor 116 may be positioned in the first aperture 122 of the first attachment site 104 (e.g., slid through the aperture 122). The tongue depressor 116 may be wooden, plastic, metal, or any other type of material. The tongue depressor 116 with the tongue maneuvering apparatus 100 provides maximum control for a healthcare provider. The tongue depressor 116 coupled to the tongue maneuvering apparatus 100 may assist the healthcare provider in maintaining control of the tongue so that a patient cannot move their tongue towards the back of the throat, obscuring the view. When using the wooden tongue depressor 116 in tandem with the tongue maneuvering apparatus 100, the healthcare provider only needs to use one hand, which allows their other hand to complete the necessary procedure. However, it will be appreciated that the use of the tongue depressor 116 is not required.

Figure 10:
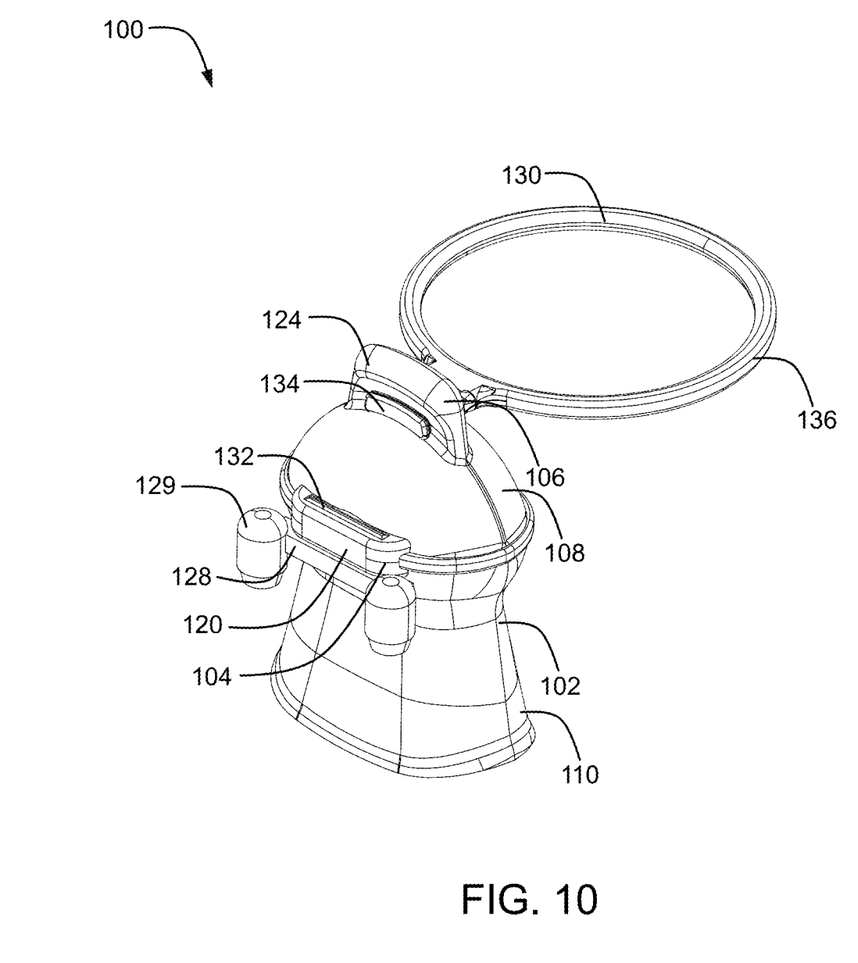
FIG. 10 illustrates a top, front perspective view of a tongue maneuvering apparatus with an illumination device coupled to a first attachment site and an anchor device coupled to a second attachment site.

As illustrated in FIG. 10, in one embodiment, the tongue maneuvering apparatus 100 comprises an illumination device 128 and an anchor device 130 that are couplable to the first and second attachment sites 104, 106, respectively. The illumination device 128 may comprise a first coupler 132 for coupling to the first attachment site 104. The first coupler 132 is shaped in a flat, square form in order to be received by the first aperture 122 of the first attachment site 104. The first coupler 122 may have a lip on one end for preventing unintended withdrawal of the illumination device 128 from the aperture 122. Alternatively, the illumination device 128 may couple to the first attachment site 104 or body 102 via a snap button, hook and loop, strap, tongue and groove, or any other attachment mechanism. Further, it will be appreciated that the illumination device 128, in one embodiment, may be permanently coupled to the body 102, forming a single unit. The illumination device 128 may comprise one or more LEDs 129 or any other light source, that are activated by the healthcare provider through, for example, a switch or a button. In one embodiment, the first aperture 122 could also be used to hold a combination tongue depressor with a light source attached thereto. The illumination device 128 illuminates the mouth and the back of the throat for the healthcare provider while leaving one hand free to perform the procedure. In the prior art, a healthcare provider would have a wooden tongue depressor in one hand and a light in the other, leaving no hands free to swab the throat or perform other procedures.

Figure 11:
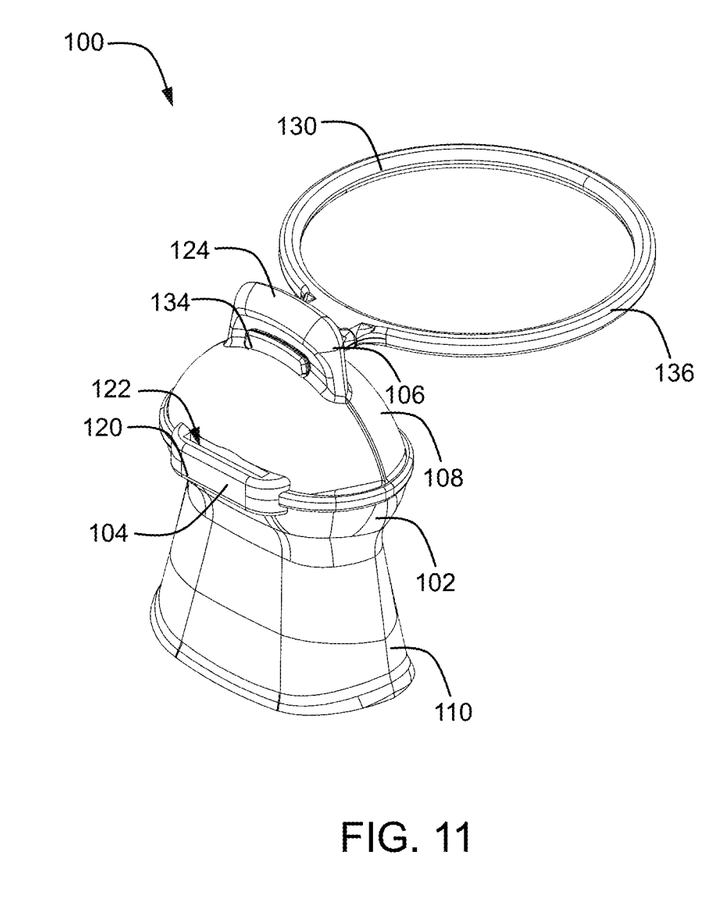
FIG. 11 illustrates a top, front perspective view of a tongue maneuvering apparatus with an anchor device coupled to a second attachment site.
Figure 12:
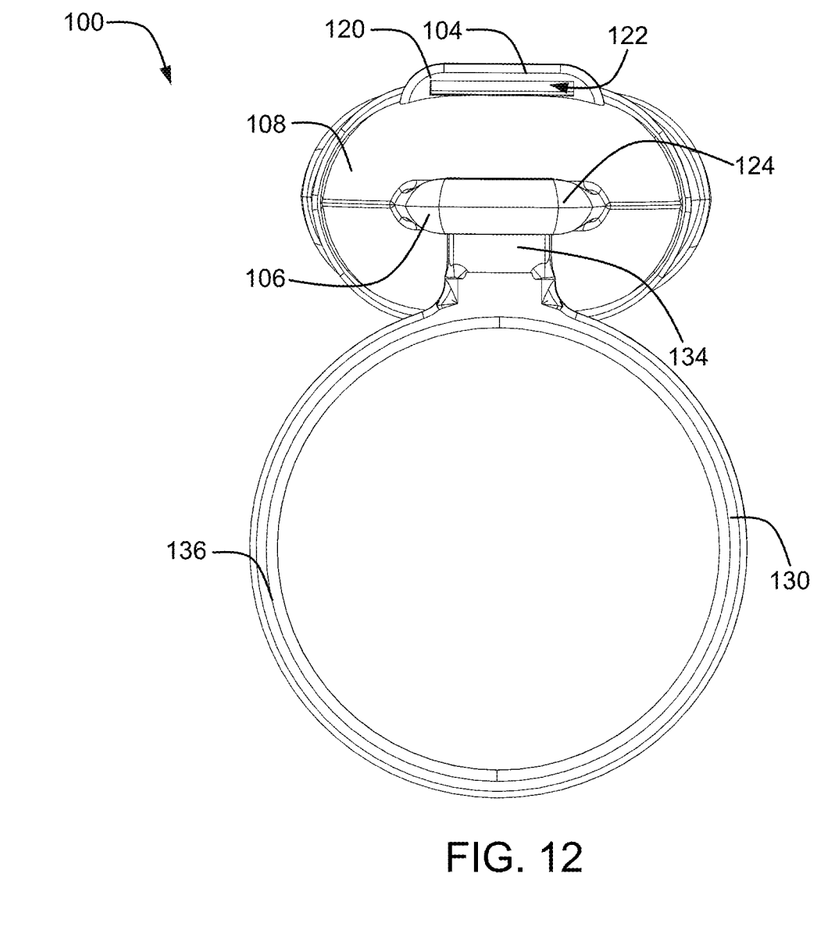
FIG. 12 illustrates a front elevation view of a tongue maneuvering apparatus with an anchor device coupled to a second attachment site.
Figure 13:
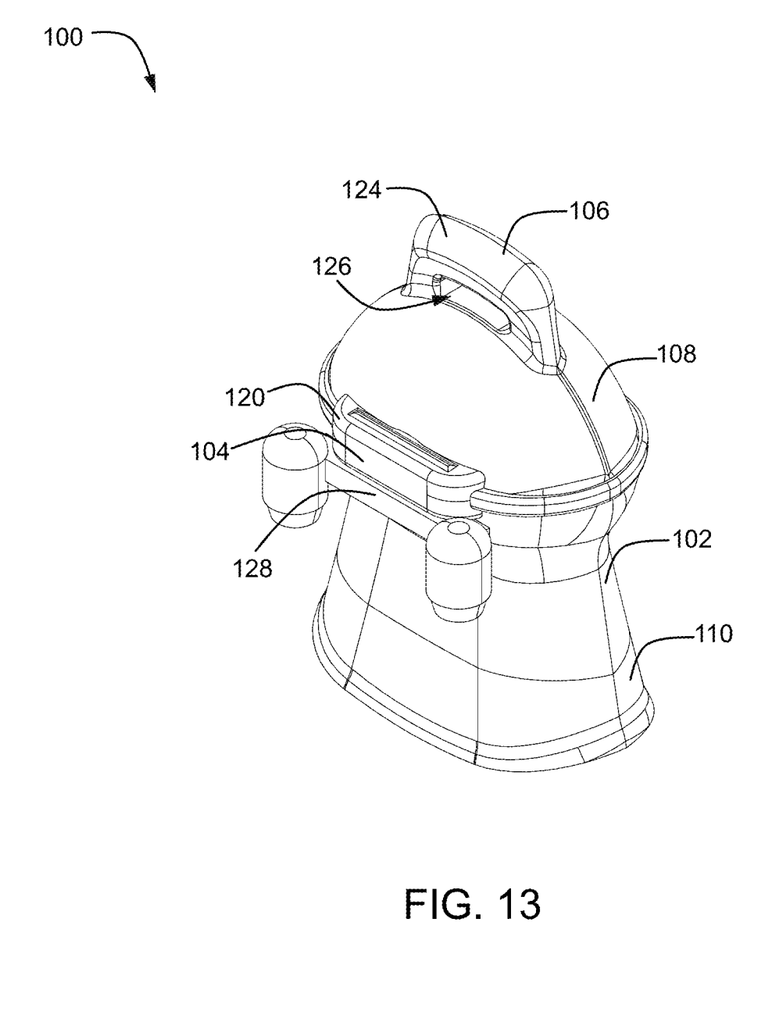
FIG. 13 illustrates a perspective view of a tongue maneuvering apparatus with an illumination device coupled to a first attachment site.

The anchor device 130 may be a ring 136. The anchor device 130 comprises a second coupler 134 and may be removably attachable to the second aperture 126 on the second attachment site 106 (e.g., male/female attachment, which may include a lip to prevent unintended withdrawal of the coupler 134 from the aperture 126). The anchor device 130 may be a silicone or a rubber ring, or a string like substance that could be tied. The anchor device 130 may couple to a patient's chin, neck, jaw, or any other location to hold the tongue maneuvering apparatus 100 in a secured position. It will be understood that the anchor device 130 may come in a variety of forms. For example, the anchor device 130 may be straps, elastics, or any other anchoring material. The anchor device 130 allows a healthcare provider to use both hands when performing a procedure, especially when help from others is limited. In the prior art, it is necessary to have help, or the healthcare provider will have to proceed with one hand, which can limit the efficacy of certain tests. It should be noted that the tongue maneuvering apparatus 100 need not be used in combination with the illumination device 128, as shown in FIGS. 11-12. Likewise, the illumination device 128 may also be used separately, as shown in FIG. 13. The anchor device 130, illumination device 128, and tongue depressor 116 can be used in a number of configurations on the tongue maneuvering apparatus 100, in combination, or not at all.

In one embodiment, a method of using the tongue maneuvering apparatus 100 comprises placing a patient's tongue into the tongue aperture 112, displacing the air in the tongue maneuvering apparatus 100. Once the tongue is inserted, the tongue maneuvering apparatus is slid toward the back of the throat, on the tongue, until the frenulum is positioned in slot 114, thereby allowing proper suction of the tongue. After the tongue maneuvering apparatus is secured, a healthcare provider may grip the body 102, bulb 108, or second attachment site 106 to move the tongue to a desired position to view the throat of the patient. If the healthcare provider needs light to illuminate the throat, the healthcare provider may couple an illumination device 128 to the first aperture 122. In some circumstances, the healthcare provider may need more control of the patient's tongue or may need to secure the tongue in place to use both hands during a procedure, which may require coupling a tongue depressor 116 to the first aperture and an anchor device to a second aperture 126. Using a tongue depressor 116 allows a provider to pull the tongue forward, out of the mouth, while simultaneously depressing the tongue for a better view, all without gagging the patient and while only requiring one hand, which is a significant improvement over the prior art.

It will be appreciated that the tongue maneuvering apparatus 100 gives more tongue control to a healthcare provider than the wooden tongue depressor known in the prior art by using suction to control the tongue. The tongue maneuvering apparatus 100 also allows a healthcare provider to use an illumination device 128 to illuminate the mouth and throat as well as an anchor device 130 to prevent movement of the tongue maneuvering apparatus 100. It will be appreciated that the patient may also grip the anchor device 130 to allow the provider to use two hands. If the healthcare provider needs to depress the tongue more than normal, the provider may use the tongue maneuvering apparatus 100 in tandem with the tongue depressor 116. Accordingly, the tongue maneuvering apparatus provides more control of the tongue and allows a healthcare provider the freedom to perform a procedure.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A tongue maneuvering apparatus comprising: a body for receiving and controlling movement of a patient's tongue, the body comprising: a bulb, a tongue receiving portion, a tongue aperture, wherein the tongue receiving portion starts wide at the tongue aperture and narrows as it proceeds to the bulb.

2. The tongue maneuvering apparatus of claim 1, further comprising a first attachment site with a first protrusion and a first aperture.

3. The tongue maneuvering apparatus of claim 1, further comprising a second attachment site with a second protrusion and a second aperture.

4. The tongue maneuvering apparatus of claim 1, wherein the body comprises a pliable material.

5. The tongue maneuvering apparatus of claim 4, wherein the pliable material comprises plastic material.

6. The tongue maneuvering apparatus of claim 4, wherein the pliable material comprises silicone material.

7. The tongue maneuvering apparatus of claim 1, wherein the body further comprises a slot configured to receive the frenulum of a patient.

8. The tongue maneuvering apparatus of claim 1, wherein the slot is v-shaped.

9. The tongue maneuvering apparatus of claim 1, further comprising a tongue depressor coupleable to a first attachment site.

10. The tongue maneuvering apparatus of claim 1, further comprising an illumination device coupleable to a first attachment site.

11. The tongue maneuvering apparatus of claim 10, wherein the illumination device comprises a first coupler for attaching to the first attachment site.

12. The tongue maneuvering apparatus of claim 10 wherein the illumination device comprises one or more LEDs.

13. The tongue maneuvering apparatus of claim 1, further comprising an anchor device coupleable to a second attachment site.

14. The tongue maneuvering apparatus of claim 13, wherein the anchor device comprises a second coupler for attaching to the second attachment site.

15. A tongue maneuvering apparatus comprising: a body for receiving and controlling movement of a patient's tongue, the body comprising: a bulb, a tongue aperture, a tongue receiving portion configured to receive the patient's tongue, a slot configured to receive the frenulum of the patient; a first attachment site comprising a first protrusion with a first aperture; a second attachment site comprising a second protrusion and a second aperture, wherein the second attachment site provides a location for a healthcare provider to grasp the tongue maneuvering apparatus, wherein the tongue receiving portion starts wide at the tongue aperture and narrows as it proceeds to the bulb.

16. The tongue maneuvering apparatus of claim 15, further comprising a tongue depressor coupleable to the first attachment site.

17. The tongue maneuvering apparatus of claim 15, further comprising an illumination device coupleable to the first attachment site.

18. The tongue maneuvering apparatus of claim 17, wherein the illumination device comprises one or more LEDs.

19. The tongue maneuvering apparatus of claim 15, further comprising an anchor device coupleable to the second attachment site.

* * * * *